United States Patent [19]

Bacich et al.

[11] Patent Number: 4,990,138

[45] Date of Patent: Feb. 5, 1991

[54] CATHETER APPARATUS, AND COMPOSITIONS USEFUL FOR PRODUCING SAME

[75] Inventors: Steven R. Bacich, Laguna Niguel; Ronald J. Jabba, Newport Beach; Manouchehr Miraki, Santa Ana; Robert Skribiski, Irvine; Louis Seiler, Jr., Huntington Beach; Robert L. Wilcox, Fullerton, all of Calif.

[73] Assignee: Baxter International Inc., Deerfield, Ill.

[21] Appl. No.: 381,895

[22] Filed: Jul. 18, 1989

[51] Int. Cl.$^5$ ............................................. A61M 29/00
[52] U.S. Cl. .................................... 604/96; 604/271
[58] Field of Search ................. 604/103, 102, 101, 96, 604/280, 264, 271, 273; 128/344

[56] References Cited

U.S. PATENT DOCUMENTS

| | | |
|---|---|---|
| 3,498,286 | 3/1970 | Polanyi et al. . |
| 3,585,707 | 6/1971 | Stevens . |
| 3,598,126 | 8/1971 | Hoeltzenbeim . |
| 3,618,614 | 11/1971 | Flynn . |
| 4,043,345 | 8/1977 | Kramann et al. . |
| 4,044,765 | 8/1977 | Kline . |
| 4,271,839 | 6/1981 | Fogarty et al. . |
| 4,283,447 | 8/1981 | Flynn . |
| 4,385,635 | 5/1983 | Ruiz . |
| 4,419,095 | 12/1983 | Nebergall et al. . |
| 4,425,919 | 1/1984 | Alston, Jr. et al. . |
| 4,479,497 | 10/1984 | Fogarty et al. . |
| 4,531,943 | 7/1985 | Van Tassel et al. . |
| 4,551,292 | 11/1985 | Fletcher et al. . |
| 4,563,181 | 1/1986 | Wijayarathna et al. . |
| 4,574,173 | 3/1986 | Bennett . |
| 4,577,543 | 3/1986 | Wilson . |
| 4,596,563 | 6/1986 | Pande . |
| 4,636,346 | 1/1987 | Gold et al. . |
| 4,639,252 | 1/1987 | Kelly et al. . |

Primary Examiner—John D. Yasko
Attorney, Agent, or Firm—Sandra S. Schultz; Michael C. Schiffer

[57] ABSTRACT

An everting balloon catheter having a distal end opening defined by a beveled rim is disclosed. The distal end portion of a catheter, e.g., an everting balloon catheter, can be made radioopaque by bonding a distal end portion comprising a polymeric material doped with a major amount of radioopaque metals onto a catheter body. Alternately, a composition comprising polymeric adhesives, and/or precursors of polymeric adhesives, and a major amount of radioopaque metal components can be placed, e.g., painted on the distal end portion of a catheter body to provide the desired degree of radioopacity.

37 Claims, 3 Drawing Sheets

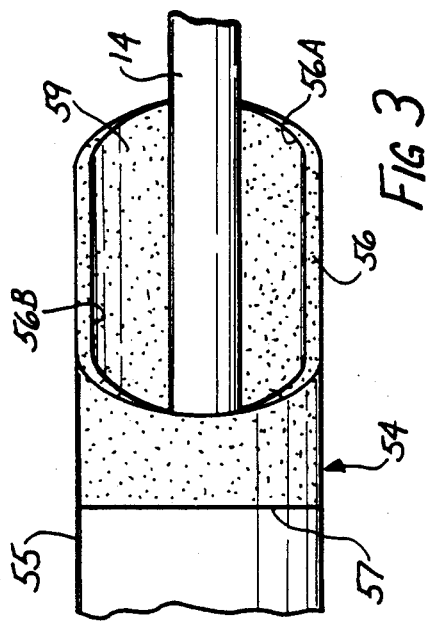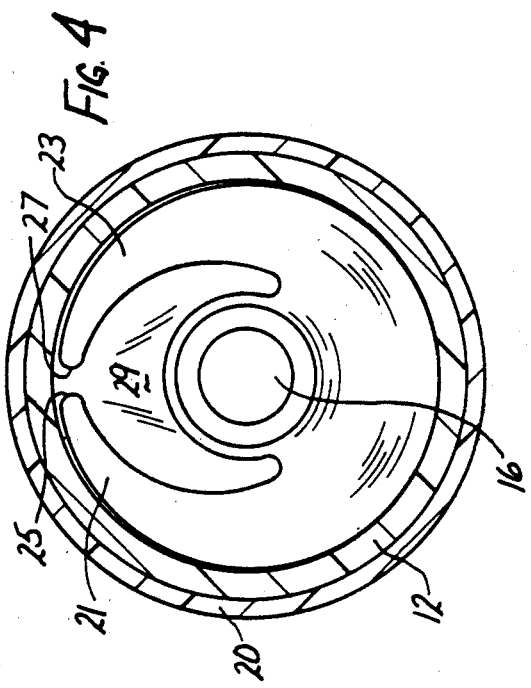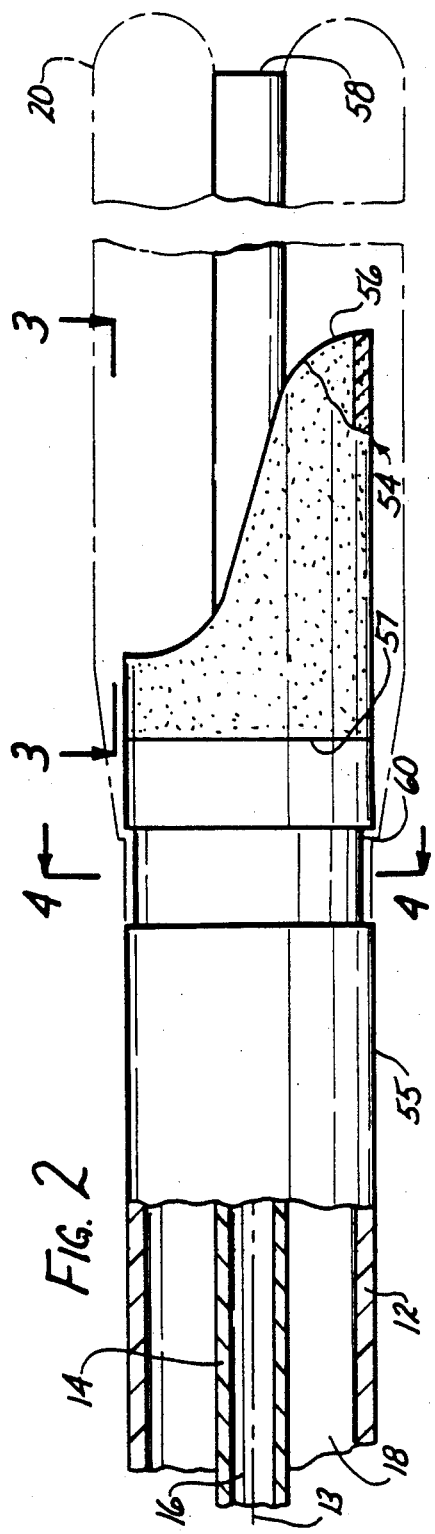

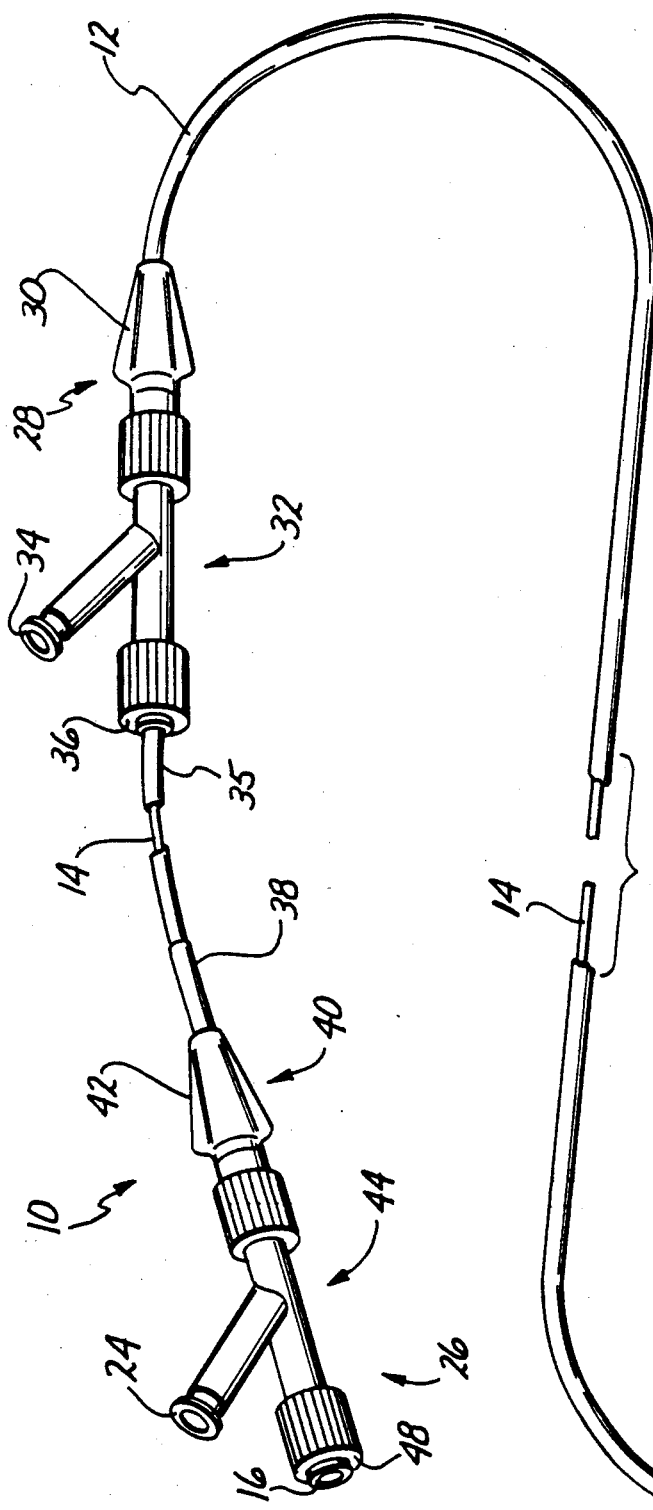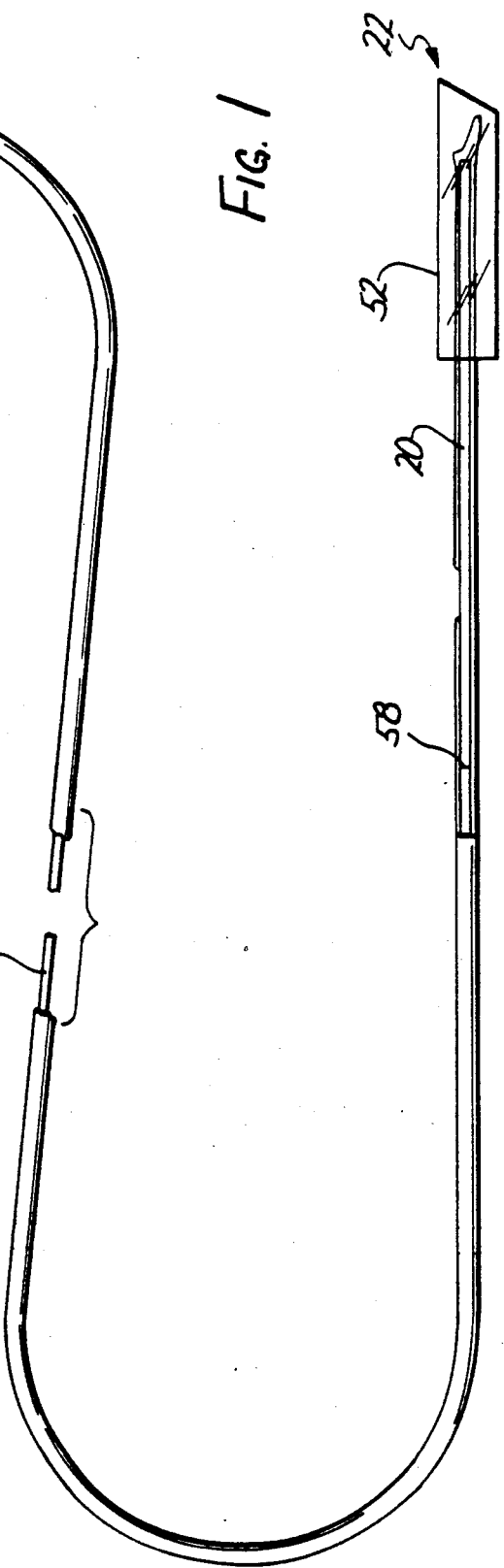
FIG. 1

CATHETER APPARATUS, AND COMPOSITIONS USEFUL FOR PRODUCING SAME

BACKGROUND OF THE INVENTION

The present invention relates to catheters for insertion into the body of a patient, and to compositions useful for producing such catheters. More particularly, the invention relates to such catheters, for example, linear everting balloon catheters, which are relatively easy to produce, relatively easy to insert, and are effective when inserted into the patient's body.

Medical catheters often must pass through tortuous paths in a patient's body before arriving at the desired location. Much difficulty, and discomfort and even danger to the patient, is frequently encountered in manipulating such catheters in the patient's body. The presence of guidewires does not resolve this problem. For example, previous everting balloon catheters, e.g., useful in angioplasty procedures, tend to perform in a less than desired manner in terms of tracking along a guidewire. The distal end or tip of the catheter body is too stiff and the inverted balloon catheter system does not allow easy guidewire movement.

Another problem which arises in using certain catheters is the need to know quite precisely where the catheter is in the patient's body. Conventional fluoroscopy procedures have teen used to visualize catheters in the body. These catheters have bands of heavy, radioopaque metal at or near the distal end of the catheter to facilitate such visualization. Such radioopaque metal bands do present certain difficulties. For example, such bands involve an additional manufacturing step. Also, if the bands are away from the distal tip of the catheter body, the precise location of the distal tip is not readily apparent On the other hand, if the bands are located at the distal tip of the catheter body, they may interfere with the functioning of the catheter.

SUMMARY OF THE INVENTION

New catheter apparatus have been discovered. One substantial advantage of the present invention is the provision of catheters having relatively flexible distal end portions The present catheters are able to be effectively manipulated through tortuous paths and/or to follow or track the path of a guidewire in the patient's body. The present invention is particularity useful in linear everting balloon catheters. In such everting balloon catheters, the present invention provides a further unexpected and fortuitous effect on the folding system of the balloon as it is inverted into the body of the catheter during preparation for clinical use. Thus, as the balloon is inverted through the distal end or tip of the outer catheter shaft, the balloon is preferably folded into a clamshell pattern that both efficiently packs the balloon in the catheter shaft, which decreases frictional resistance to the inversion of the balloon and, in addition, allows a central channel to be effectively maintained through the inverted balloon so that the guidewire can be effectively passed and manipulated through the inverted balloon/catheter system.

Another important advantage provided by the present invention allows for a more precise fluoroscopic visualization of the catheter in the patient's body. This effective visualization is obtained without having any detrimental effect on the effectiveness of the functioning of the catheter. Further, such visualization is provided relatively easily so that manufacturing economies are obtained.

In describing the present invention, reference is made primarily to an everting balloon catheter. However, it should be noted that the present invention is useful in various catheter systems other than everting balloon catheters.

In one broad aspect the present invention is directed to an everting balloon catheter which includes a flexible, elongated tubular catheter body or shaft sized and adapted to be inserted into the body, e.g., vascular system, of a patient. This catheter body has a distal end portion and a body portion located proximally of the distal end portion. The catheter body also includes a distal end opening. A balloon means capable of being inverted into the body and of being everted therefrom is included. The present improvement comprises a rim defining the distal end opening of the catheter body which is beveled, as defined herein. This beveled rim provides for increased flexibility of the distal end portion of the catheter body relative to the body portion of the catheter body. In addition, this beveling preferably provides for improved folding of the balloon as it is inverted into the catheter body.

The rim defining the distal end opening of the catheter body is beveled. That is, the rim includes one or more points which are circumferentially spaced away from the distal most point or points of the rim and which are proximal of such distal most point or points. The distal most circumferentially spaced apart points at least two locations on the rim are also axially spaced apart. The rim can be a line or a surface. In one embodiment, this beveled rim, when viewed in axial profile (i.e., when viewed in profile in a direction perpendicular to the longitudinal axis of the catheter body), forms a substantially straight line inclined from the longitudinal axis of the catheter body, preferably so inclined at an angle in the range of about 5° to about 45°. The beveled rim may, when viewed in axial profile, form a curve, in particular a substantially symmetrical curve, from its proximal most point or points to its distal most point or points.

In one embodiment, the distal end portion of the catheter body is preferably radioopaque, i.e., has a substantial degree of radioopacity. This feature allows the catheter to be visualized, i.e., using conventional fluoroscopic techniques, in the patient's body for placement in the patient's body.

Another broad aspect of the present invention provides a composition comprising an intimate, preferably substantially uniform, admixture of a polymeric material and a radioopaque substance which is located, e.g., coated, on at least a portion of the distal end portion of a catheter body or shaft. This composition is present in an amount effective to provide a substantial degree of radioopacity to at least a portion of the distal end portion of the catheter body or shaft.

The polymeric material included in the composition is preferably compatible with, e.g., able to adhere to, the distal end portion of catheter body or shaft, which itself is preferably made of one or more polymers. In a particularly useful embodiment, the polymeric material employed is selected from polymeric adhesives, precursors of polymeric adhesives and mixtures thereof. Any suitable polymeric adhesive may be employed in the presently useful compositions. Among the useful polymeric adhesives are those which are capable of adhesively bonding to a polyolefin substrate. Examples of useful polymeric adhesives include polyurethanes, epoxy resins, polycyanoacrylates, ethylene vinyl acetate copolymers and the like and mixtures thereof.

The radioopaque substance included in the composition may be any substance, such as those conventionally used, which provides the distal end portion of the catheter with a substantial degree of radioopacity. The radioopaque substance is preferably selected from the group consisting of radioopaque metal components and mixtures thereof, in particular radioopaque elemental metals and mixtures thereof, e.g., in the form of metal particles. Examples of such metals include gold, the platinum group metals, tungsten, molybdenum, rhenium, tantalum and mixtures thereof, with tantalum being particularly useful. The amount of radioopaque substance to be used in the present compositions is chosen based upon the amount of or degree of radioopacity desired. Although relatively minor amounts of radioopaque substance may be used, it is preferred to have the composition comprise a major amount, i.e., at least 50% by weight, of radioopaque substance and a minor amount of polymeric material, i.e., less than 50% by weight, of the total radioopaque substances and polymeric material present in the composition. This feature reduces the total amount of composition required to be used while providing the desired degree of radioopacity.

The presently useful composition is preferably applied, e.g., by painting, dipping and the like, to the distal end portion of the catheter body in the form of a liquid-solid slurry. One or more volatile liquid carriers, e.g., solvents for the polymeric material and/or precursors of the polymeric material employed, may be included in the mixture which is applied. After application, the composition is solidified, e.g., by evaporation of the carriers, and/or polymerization of the precursors of the polymeric material, and/or other means, to form the final radioopaque composition, e.g., coating on the distal end portion of the catheter body.

In a particularly useful embodiment, the distal end portion of the catheter body or shaft has an exterior surface, and the composition is located on at least a portion of this exterior surface. The composition may be adhesively bonded to the distal end portion.

A further broad aspect of the invention involves a catheter which includes a distal end element located distally of the proximal portion of the catheter body or shaft. This distal end element is made of a combination comprising an intimate, preferably substantially uniform, admixture of a polymeric material and a radioopaque substance present in an amount effective to provide a substantial degree of radioopacity to the distal end element. The distal end element is preferably bonded to the proximal portion of the catheter body or shaft, and like the proximal portion of the catheter body preferably includes a through lumen, which is more preferably substantially aligned with the through lumen of the proximal portion of the catheter body. This distal end element is preferably pre-formed, e.g., by extrusion, before being secured to the proximal portion of the catheter body. The rim defining the distal end opening of this distal end element may be blunt or, and preferably, it may be beveled distal end, as described herein.

The polymeric materials and radioopaque substances described herein with regard to the compositions may also be used in the present combinations. The primary difference between the present compositions and combinations is that the compositions are located on, e.g., coat, the distal end portion of the catheter body, while the combinations actually form the distal end portion of the catheter body. Because of this difference, certain polymeric materials and radioopaque substances may be useful in one, but not both, of the present compositions and combinations. For example, certain of the present compositions may be useful for coating the distal end portion of a catheter body, but may not be formable, e.g., extrudable, into the distal end portion of the catheter body itself. A particularly useful polymeric material which may be used in both the present compositions and combinations is selected from copolymer of olefins, in particular ethylene and vinyl acetate, and mixtures thereof. Preferably, the copolymer contains about 1 to about 51 percent vinyl acetate monomer units, more preferably about 10 to about 30 percent vinyl acetate monomer units, and still more preferably about 18 percent vinyl acetate monomer units.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is an overall view of one embodiment of the catheter of the present invention with cut-away section of the distal end portion showing the catheter balloon fully inverted FIG. 2 is an axial plan view, partly in cross-section, of the distal end area of the catheter shown in FIG. 1 with the balloon, shown in shadow, being fully inflated and everted.

FIG. 3 is a plan view taken generally along line 3—3 of FIG. 2.

FIG. 4 is a cross-sectional view taken generally along line 4—4 of FIG. 2 with the balloon show fully inverted.

DETAILED DESCRIPTION OF THE DRAWINGS

Figure 5:
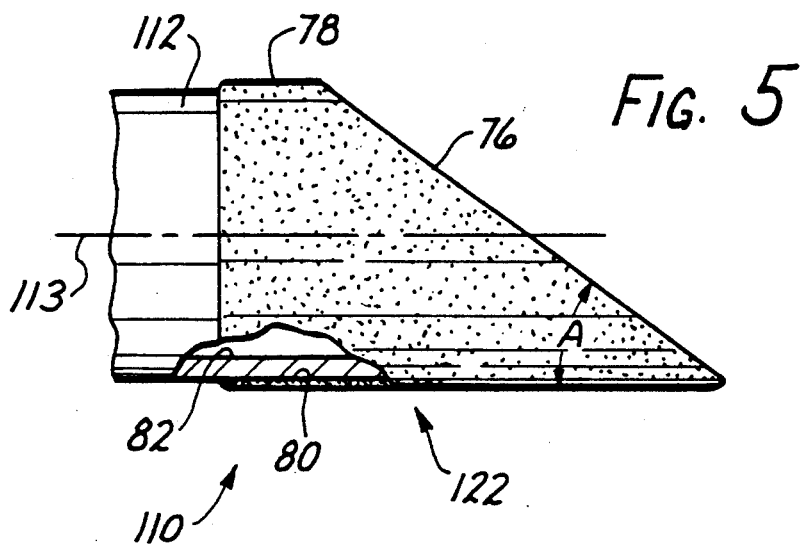
FIG. 5 is an axial plan view, partly in cross-section, of the distal end area of an alternate embodiment of the present outer catheter tube.

Referring now to FIGS. 1 and 2, an everting balloon catheter, shown generally as 10, is a dilatation catheter including an outer tube 12 about 0.06 inches in outer diameter and about 135 cm. in length defining a central axis 13. The catheter 10 has a central or inner tube 14 coaxial with the outer tube 12 to form a double lumen catheter preferably about 150 cm. long, one lumen 16 (the inner or "through-lumen") axially disposed within the other lumen 18. The through-lumen 16 as long as the outer tube 12 plus the length of balloon 20, although additional length can be added for easy maneuverability during eversion and reinversion. The through-lumen 16 is open to the environment distally and inner tube 14 is preferably about 0.02 inches in inner diameter and about 0.028 inches in outer diameter. The through-lumen 16 allows use of the catheter 10 over a guidewire, and, via injection port 24, can be used to inject dyes, contrast media, saline, or other fluids into the system.

The catheter 10 terminates at proximal end 26 in an outer hub 28 with wings 30. The outer hub 28 is attached to an outer Y-connector 32 having an inflation port 34 accessing outer lumen 18. Through an "O" ring 36 sealing outer lumen 18 from the environment at the proximal end, inner tube 14 slidably extends proximally from outer hub 28 to terminate in a sleeve 38 surrounding by an inner hub 40 having wings 42 and attached to an inner Y-connector 44 including injection port 24 which accesses the through-lumen 16. Access to the through-lumen 16 at the proximal end is gained through an "0" ring 48 which can form a seal.

Sleeve 3B is usually formed of heatshrunk polyvinyl chloride ("PVC") and the two hubs 28 and 40 related adapters are usually formed of polycarbonate or PVC.

Except for the distal end segment 54 to be discussed hereinafter, the outer tube 12 and the inner tube 14 of catheter 10 are made of polyethylene. The primary considerations for the material for the tubes 12 and 14 are, of course, biological inertness, inertness to saline, contrast media and other materials to be infused through the tubing, and sufficient flexibility, resistance to deformity, and torquability to bend the catheter 10 through the tortuous pathways of the vascular or any other system in which it will be used without crimping or occlusion.

The catheter 10 is stored in sterile condition before use by a cover or protective sleeve 52 over the distal end region 22.

Outer tube 12 includes a distal end segment 54 which is radioopaque and includes a beveled distal rim 56 which defines a distal end opening 59 of outer tube 12. This beveling is further illustrated by considering points 56A and 56B. Points 56A and 56B are circumferentially spaced apart and are the distal most points at two locations on rim 56. Point 56A is distal of point 56B. Thus, rim 56 is beveled. Distal end segment 54 is bonded to the proximal portion 55 of outer tube 12. For the sake of illustration, this bond is shown as a single line 57 in FIG. 2, although it is preferred that this bond involve a finite bonding area. Such bonding may be accomplished through the use of adhesives, the application of heat or the like. The inside and outside diameters of distal end segment 54 are substantially the same as the corresponding parameters of the proximal portion 55 of outer tube 12.

As shown in FIG. 2, distal rim 56 is beveled so that the axial profile of distal rim 56 (a profile taken in a direction perpendicular to longitudinal axis 13 of catheter 10) is a symmetrical curve. This beveling provides increased flexibility to the distal end portion of catheter 10 and, in addition, promotes or facilitates the advantageous folding of balloon 20 upon inversion of balloon 20 into outer tube 12.

This advantageous folding of balloon. 20 is illustrated with reference to FIG. 4. Upon deflation and reinversion, balloon 20 forms two longitudinally extending wings 21 and 23. Beveled distal rim 56 facilitates folding balloon 20 into a "clamshell" configuration, as shown in FIG. 4, with each of the balloon's wings 21 and 23 extending toward its distal end, 25 and 27 respectively, in mutually substantially opposing circumferential directions. This "clamshell" folding of balloon 20 efficiently, e.g., from a use-of-space standpoint, packs balloon 20 in outer tube 12, and forms a substantially centrally located longitudinally extending open space 29 through which a guidewire from through-lumen 16, can be easily passed. Without such folding, the inverted balloon may create resistance to the passage through the catheter, or even block the passage, of the guidewire.

Distal end segment 54 is made, preferably extruded, from a material which is compatible with, e.g., able to be bonded to, the proximal portion 55 of outer tube 12, and is radioopaque. One particularly useful material of construction for distal end segment 54 is a mixture of ethylene vinyl acetate copolymer and tantalum Ethylene vinyl acetate is a hot melt adhesive not now believed to be used for catheter tips. Other possible polymers are those which may accept high loadings of radiopaque materials, and other radiopaque materials may be used, such as bismuth, barium, gold, and titanium, molybdenum, rhenium, and the platinum group metals. In the preferred mixture, about 50 to 75 percent by weight, most preferably preferably 75 percent by weight, tantalum (powder) is used together with 25 weight percent ethylene vinyl acetate. The ethylene vinyl acetate copolymer usually contains from about 5 to about 51 weight percent vinyl acetate, the remainder being ethylene units. The preferred ethylene vinyl acetate copolymer is about 82 weight percent ethylene and 18 weight percent vinyl acetate.

When inner tube 14 is in its fully withdrawn position, its distal end 58 usually terminates up to about 15 cm. back from the beveled distal rim 56. The exact distance from end 56 will vary with the particular purpose for which the catheter 10 is designed and the length of the expected occlusion in the blood vessel. Thus, in models of catheter 10 for use in the coronary arteries inner tube 14 may terminate about 2 to 4 cm. back, while in peripheral models inner tube 14 may terminate 10 cm. or more back.

One end of tubular balloon 20 is attached to the periphery of inner tube 14 at the distal end thereof. The outer end of the balloon 20 is attached to the exterior of outer tube 12 spaced back from the distal end segment 54, in an annular recession 60 in the exterior of the outer tube 12. The balloon 20, which is preferably made of an ethylene vinyl acetate copolymer is bonded to recession 60, e.g., using adhesives or the application of heat. In some instances, balloon 20 may be textured on the surface to promote anchoring at the desired spot in the blood vessel.

When inner tube 14 is completely withdrawn, the balloon 20 remains substantially inside the outer tube 12 When inner tube 14 is moved distally, it causes the balloon 20 to evert and aids balloon inflation when saline is simultaneously infused through the inflation port 34 to inflate the balloon 20.

The material used in the balloon 20 has sufficient strength to sustain the pressures required for dilatation, usually about 10 to 12 atmospheres.

To make the catheter 10, the balloon material is extruded to form tubing and irradiated with electron-beam radiation in the fashion used for cross-linking standard balloons. The balloons are then blown and cut to size.

The inner tubing material is also extruded and cut to size, and the balloon bonded to the outer distal tip thermally or preferably by using biocompatible adhesives such as a polycyanoacrylate adhesive or a polyurethane adhesive. A mandril is passed into the balloon which is inverted by hand rolling its open end back over the mandril and around the inner tube.

Tubing from which the proximal portion 55 of outer tube 12 is made, and tubing from which the distal and segment 54 of outer tube 12 is made, are compounded, extruded and cut. These two lengths of tubing are bonded together, e.g., in a conventional manner such as by the application of heat to the overlapped ends of the lengths of tubing.

The bevel distal rim 56 is then cut from the distal end of the bonded tube.

Using hollow stainless steel tubing as support, the inner tube 14 is backloaded into the outer tube 12 (the bonded tube) and the balloon 20 is bonded to the outer tube by heatshrinking or the application of adhesives. In one embodiment, heat is applied to the outer tube 12 to create recession 60 and a biocompatible adhesive used to attach the balloon.

An intermediate sleeve 35 is heatshrunk about the proximal portion of inner tube 14 to provide inner tube 14 with increased stiffness. Sleeve 38 is then heatshrunk about the proximal end of the intermediate sleeve 35 and the outer hub 28 is attached to the outer tube 12 using an ethylene vinyl acetate polymeric adhesive, followed by the outer Y connector 32, the inner hub 42 and the inner Y connector 44. The package is inspected and finally sterilized and sold.

In operation, the catheter 10, with balloon 20 inverted, is introduced into the vascular system, usually via a guiding catheter, particularly when used for percutaneous coronary access. Where it will be inserted only into peripheral vessels or is inserted intraoperatively, usually no guiding catheter is used, although a guidewire can be used through the through-lumen 16.

The distal end segment 54 of the catheter 10 is inserted as close as possible to the lesion to be removed, under fluoroscopy, and the balloon 20 is inflated with saline through the inflation port 34 to about 2 atmospheres. The precise placing of catheter 10, under fluoroscopy, is advantageously facilitated since the entire distal end segment 54 is radioopaque. Thus, under fluoroscopy, one is able to effectively visualize the distal end segment 54 of catheter 10. In addition, the beveled distal rim 56 renders the distal portion of outer tube 12 more flexible than the proximal portion 55 of outer tube 12. This increased flexibility facilitates inserting catheter 10 into the vascular system. Inner tube 14 is slid distally to evert the balloon 20 until resistance is felt, indicating that the balloon has formed an anchor annulus. If the distal end segment 54 continues to move, however, the catheter 10 is insufficiently anchored, and the balloon 20 is inflated further until the anchor annulus is formed. The more compliant the balloon material, the lower the amount of pressure required to form the anchor annulus. Silicone texturing on the exterior of the annulus may further help to anchor the catheter 10.

Pushing the inner tube 14 distally, the balloon 20 is then further everted to extend it until it crosses the stenosis. At that point, dilatation (or any diagnostic purpose for which the catheter 10 is inserted) is handled in the standard manner. When the process is finished, the balloon 20 is deflated (via the inflation port) and the catheter withdrawn, or the balloon 20 is reinverted after the catheter is withdrawn by pulling the inner tube 14 proximally. One important feature of the present invention is illustrated in FIG. 4. The beveled distal rim 56 facilitates the clamshell folding of balloon 20 upon inversion into outer tube 12. This folding forms a central channel through outer tube 12 which allows the guidewire in through-lumen 16 to move with reduced resistance.

Figure 6:
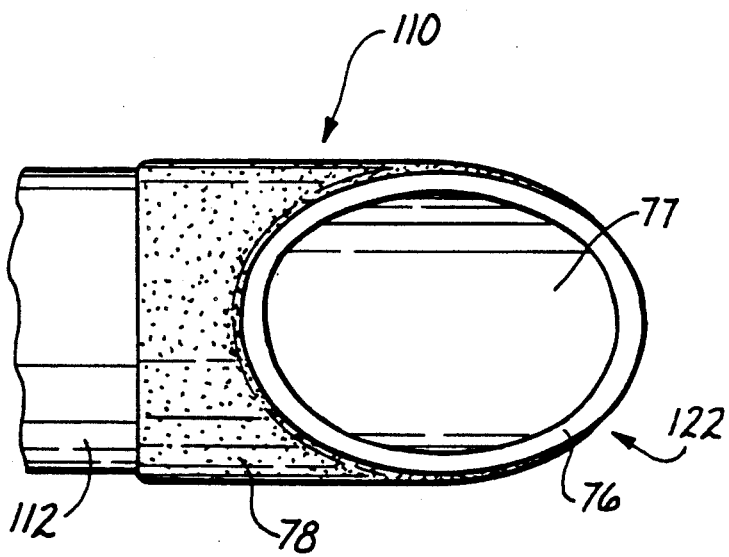
FIG. 6 is a plan view taken generally above line 6—6 of FIG. 5.

FIG. 5 and 6 show an alternate embodiment of the present catheter. Except as expressly noted below, this alternate everting balloon catheter, shown generally as 110, is structured and functions substantially similarly to catheter 10. Components of alternate catheter 110 which correspond to components of catheter 10 are given corresponding reference numerals increased by 100.

The primary difference between catheter 10 and alternate catheter 110 involves distal end region 122 of alternate catheter 110. Outer tube 112, instead of terminating proximally of the distal end of the catheter as in catheter 10, terminates distally in a beveled distal rim 76 defining distal opening 77. The beveling of distal rim 76 forms a straight line (i.e. is linear) in axial profile (when viewed in a direction perpendicular to longitudinal axis 113) which forms an angle A preferably in the range of about 5° to about 45°, for example, about 30°.

In addition, distal end region 122 includes a radioopaque coating 78 which renders the distal end region 122 of alternate catheter 110 radioopaque under fluoroscopy. The coating is made from a composition including an adhesive carrier such as urethane, cyancacrylate, or epoxy, for example, and preferably polyurethane. The composition also includes a radiopaque material such as a heavy metal or inorganic compound thereof, such as those listed above for use in forming distal end segment 54. Generally, the radiopaque material is present in amounts of about 50 to 90 percent by weight, and the composition is formed as a liquid-solid slurry. The composition may also include a liquid carrier, which is later evaporated away, to facilitate painting radioopaque coating 78 on outer tube 112. It may be desirable, or even necessary, to apply more than one layer of the liquid solid slurry to obtain the desired thickness of coating 78, and, thus, the desired degree of radiopacity for the alternate catheter 110. Radioopaque coating 78, which is preferably adhesively bound to outer tube 112, may alternately or in addition be placed on the interior surface 82 of outer tube 112, although it is preferred to coat the exterior surface 80 and not the interior surface 82. The coating can be advantageously painted on the outer tube to use as an adhesive which then bonds the balloon to the catheter.

In any event, alternate catheter 110 functions in substantially the same manner as catheter 10 and provides substantially the same advantageous results. Thus, the beveled distal rim 76 of outer tube 114 provides increased flexibility to the distal end region 122 relative to the proximal portion of alternate catheter 110. This increased flexibility allows alternate catheter 110 to be easily maneuvered through the tortuous part of a patient's vascular system. In addition, the beveled distal rim 76 of alternate catheter 110 facilitates the advantageous clamshell folding of the balloon of alternate catheter 110 as described above with reference to catheter 10. Moreover, the radioopaque coating 78 renders the distal end region 122 of catheter 110 radioopaque, under fluoroscopy. This allows for proper and precise placement of alternate catheter 110 in the patient's body. In addition, radioopaque coating 78 does not interfere with the functioning, e.g., balloon eversion, of alternate catheter 110.

It should be understood that the foregoing description is intended by way of illustration and not by way of limitation and that many modifications and variations are within the scope of the invention which is described by the appended claims. Furthermore, it should be noted that the invention relates to many different types of apparatus and catheters, not just dilatation catheters.

What is claimed is:

1. An apparatus for insertion into the body of a patient comprising:
   a flexible catheter tube sized and adapted to be inserted into the body of a patient;
   said catheter tube having a distal end portion and a body portion located proximally of said distal end portion;
   said catheter tube including a distal end opening defined by a rim which is beveled; and
   balloon means attached to said catheter tube and capable of being inverted in said catheter tube and of being everted therefrom.

2. The apparatus of claim 1 wherein said distal end portion has increased flexibility relative to said body portion.

3. The apparatus of claim 1 wherein said catheter tube further includes a lumen and said distal end opening is the distal termination of said lumen.

4. The apparatus of claim 1 wherein said distal end portion has a substantial degree of radioopacity.

5. The apparatus of claim 1 wherein said beveled rim facilitates the folding of said balloon means as said balloon means is inverted into said catheter tube.

6. The apparatus of claim 1 wherein said balloon means is folded into a clamshell configuration as said balloon means is inverted into said catheter tube.

7. The catheter of claim 1 wherein the beveling of said rim has a curved axial profile.

8. The catheter of claim 1 wherein the beveling of said rim has a substantially symmetrical curved axial profile.

9. The catheter of claim 1 which further includes an elongated member located at least partially within said catheter body, said member includes an open ended tubular element and said balloon means is secured to said tubular element.

10. An apparatus for insertion into the body of a patient comprising:
   a catheter tube sized and adapted to be inserted in the body of a patient;
   said catheter tube having a distal end portion and a body portion located proximally of said and distal end portion, and a lumen; and
   a composition comprising a minor amount of polymeric material, and a major amount of radioopaque substance selected from the group consisting of radioopaque metal components and mixtures thereof, said composition being located on at least a portion of said distal end portion and being present in an amount effective to provide a substantial degree of radioopacity to at least a portion of said distal end portion.

11. The apparatus of claim 10 herein said composition is present as an intimate admixture of said polymeric material and said radioopaque substance.

12. The apparatus of claim 10 wherein said radioopaque substance is selected from the group consisting of elemental radioopaque metals and mixtures thereof.

13. The apparatus of claim 10 wherein said distal end portion has an exterior surface and said composition is located on at least a portion of said exterior surface.

14. The apparatus of claim 10 wherein said composition is adhesively bonded to said distal end portion.

15. The apparatus of claim 10 wherein said radioopaque substance is selected from the qroup consisting of gold, the platinum group metals, tungsten, molybdenum, rhenium, tantalum and mixtures thereof.

16. An apparatus for insertion into the body of a patient comprising:
   a flexible catheter tube sized and adapted to be inserted into the body of a patient;
   a distal end element located distally of said catheter tube and made of a combination comprising a polymeric material and a radiopaque substance present in said combination in an amount effective to provide a substantial degree of radiopacity to said distal end element, said distal end element including a distal end opening defined by a rim which is beveled; and
   balloon means attached to said catheter tube and capable of being inverted in said catheter tube and of being everted therefrom.

17. The apparatus of claim 16 wherein said radioopaque substance is selected from the group consisting of radioopaque metal components and mixtures thereof, 18. The apparatus of claim 16 wherein said distal end element is bonded to said catheter tube.

19. The apparatus of claim 16 wherein said distal end element is formed by extrusion.

20. The apparatus of claim 16 wherein said polymeric material is selected from the group consisting of ethylene vinyl acetate copolymers and mixtures thereof, and said radioopaque substance is tantalum in the form of particles.

21. The apparatus of claim 16 wherein said distal end element has increased flexibility relative to said catheter tube.

22. The apparatus of claim 16 wherein said beveled rim facilitates the folding of said balloon means as said balloon means is inverted into said catheter tube and said distal end element.

23. An apparatus for insertion into the body of a patient comprising:
   a catheter tube sized and adapted to be inserted into the body of a patient;
   a composition comprising a polymeric material and a radioopaque substance present in said composition in an amount effective to provide a substantial degree of radioopacity adhesively bonded to said tube; and
   balloon means attached to said tube and capable of being inverted in said catheter tube, and of being everted therefrom.

24. The apparatus of claim 23 wherein said radioopaque substance is selected from the group consisting of elemental radioopaque metals and mixtures thereof.

25. The apparatus of claim 23 wherein said radioopaque substance is present in the form of elemental metal particles.

26. The apparatus of claim 24 wherein said radioopaque substance is selected from the group consisting of gold, the platinum group metals, tungsten, molybdenum, rhenium, tantalum and mixtures thereof.

27. The apparatus of claim 23 and wherein the composition is applied in the form of a liquid-solid slurry.

28. The apparatus of claim 23 wherein said polymeric materials are selected from the group consisting of polyurethanes, epoxy resins, polycyanoacrylates, ethylene vinyl acetate copolymers and mixtures thereof.

29. The apparatus of claim 23 wherein said catheter tube includes at its distal end a beveled tip and said composition is adhesively bonded to said tip.

30. Apparatus according to claim 23 and wherein said balloon means is adhesively attached to said tube using said composition.

31. The catheter of claim 1 and wherein the beveling of the rim has a linear axial profile which defines an angle from the catheter axis.

32. The catheter of claim 31 and wherein the angle is about 5 to about 45 degrees.

33. The catheter of claim 32 and wherein the angle is about 17 degrees.

34. An apparatus for insertion into the body of a patient comprising:
- a first flexible catheter tube sized and adapted to be inserted into the body of a patient, said first flexible catheter tube having a distal end portion and a body portion located proximally of said distal end portion, said first flexible catheter tube including a distal end opening defined by a rim which is beveled;
- a second flexible catheter tube sized and adapted to slide in said first flexible catheter tube, said second flexible catheter tube having a distal end portion and a body portion located proximally of said distal end portion and a body portion located proximally of said distal end portion; and
- balloon means attached to said distal end portions of said first and second catheter tubes and capable of being inverted in said first catheter tube and of being everted therefrom.

35. The apparatus of claim 34 wherein said distal end of said first flexible catheter tube includes a composition comprising a polymeric material and a radiopaque substance present in said combination in an amount effective to provide a substantial degree of radiopacity to sid distal end.

36. The apparatus of claim 35 wherein said composition forms a separate element fitted to said distal end.

37. The apparatus of claim 36 wherein said element has increased flexibility relative to said catheter tube.

* * * * *

UNITED STATES PATENT AND TRADEMARK OFFICE
CERTIFICATE OF CORRECTION

PATENT NO. : 4,990,138
DATED : Feb. 5, 1991
INVENTOR(S) : Bacich et al

It is certified that error appears in the above-identified patent and that said Letters Patent is hereby corrected as shown below:

Column 2, line 47 before "placement", insert --proper--

Column 4, line 29 after "inverted", insert --.--

Column 5, line 3 replace "surrounding" with --surrounded--

Column 5, line 9 replace "3B" with --38--

Column 6, line 6 after "tantalum" insert --.--

Column 8, line 42 replace "evert" with --event--

Column 9, claim 11, line 54 replace "herein" with --wherein--

Signed and Sealed this

Twenty-third Day of June, 1992

Attest:

DOUGLAS B. COMER

*Attesting Officer*    *Acting Commissioner of Patents and Trademarks*